(12) United States Patent
Carosella et al.

(10) Patent No.: US 6,528,304 B1
(45) Date of Patent: Mar. 4, 2003

(54) EUKARYOTIC CELLS EXPRESSING AT THEIR SURFACE AT LEAST AN HLA-G ISOFORM AND THEIR APPLICATIONS

(75) Inventors: Edgardo Delfino Carosella, Paris (FR); Jean Dausset, Paris (FR); Marek Kirszenbaum, Paris (FR); Pascale Paul, Paris (FR); Nathalie Rouas-Freiss, Paris (FR)

(73) Assignee: Commissariat A l'Energie Atomique, Paris (FR)

(*) Notice: Subject to any disclaimer, the term of this patent is extended or adjusted under 35 U.S.C. 154(b) by 0 days.

(21) Appl. No.: 09/147,166

(22) PCT Filed: Feb. 20, 1998

(86) PCT No.: PCT/FR98/00333
§ 371 (c)(1),
(2), (4) Date: Oct. 21, 1998

(87) PCT Pub. No.: WO98/37098
PCT Pub. Date: Aug. 27, 1998

(30) Foreign Application Priority Data

Feb. 21, 1997 (FR) ............................................. 97 02118

(51) Int. Cl.$^7$ ......................... C12N 5/02; C12N 15/00; C12N 15/63; C07H 21/04; A61K 48/00
(52) U.S. Cl. .................... 435/325; 435/320.1; 435/455; 536/23.1; 424/93.2
(58) Field of Search ...................... 536/23.1; 435/320.1, 435/325, 455; 424/93.2

(56) References Cited

FOREIGN PATENT DOCUMENTS

| FR | 2 717 498 | 9/1995 |
|----|-----------|--------|
| WO | 95 31472 | 11/1995 |
| WO | 96 31604 | 10/1996 |
| WO | 97 00085 | 1/1997 |
| WO | 97 96241 | 2/1997 |

OTHER PUBLICATIONS

Lanier; natural Killer Cells: From No Receptors to Too Many; 1997, Immunity vol. 6: 371–378.*
Franksson et. al.; Tumorigenicity Conferred to Lymphoma Mutant by Major Histocompatibility Complex–encoded Transporter Gene, 1993, J. Exp. Med. vol. 177: 201–205.*
Ishitani et. al. ; Alternative splicing of HLA–G transcripts yields proteins with primary structures resembling both class 1 and class 11 antigens, 1992, Proc. Natl. Acad. Sci. USA, 3947–3951.*
Fujii et. al.; A Soluble Form of the HLA–G Antigen Is Encoded by a Messinger Ribonucleic Acid Containing Intron 4, 1994, The Journal of Immunology,5516–5524.*

Schmidt et. al.; HLA–G Transgenic Mice: A Model for Studying Expression and Function at the Maternal/Fetal Interface, 1995, Immunological Reviews No. 147: 53–65.*
C.M. Schmidt et al., "Extraembryonic expression of the human MHC class I gene HLA–G in transgenic mice. Evidence for a positive regulatory region located I kilobase 5' to the start site of transcription" Journal of Immunology, vol. 151, No. 5, (1993), Bethesda, MD, US. pp. 2633–2645, XP002047493, see the whole document.
P. Moreau et al., "Soluble HLA–G molecule. An alternatively spliced HLA–G mRNA form candidate to encode it in peripheral blood mononuclear cells and human trophoblasts", Human Immunology, vol. 43 (1995), New York, NY. US, pp. 231–236, XP002046234 cited in the application, see the whole document.
L. Pazmany et al., "Protection from natural killer cell–mediated lysis by HLA–G expression on target cells" Science, vol. 274, (1996), Washington DC, US. pp. 792–795, XP002046235 cited in the application see the whole document.
E. D. Carosella et al., "HLA–G revisited" Immunology Today, vol. 17, No. 9, (1996), Amsterdam, NL., pp. 407–409, XP004034736 cited in the application see the whole document.
N.J.G. Webster et al., "The hormone–binding domains of the estrogen and glucocortocoid receptors contain an inducible transcription activation function", Cell, vol. 54, Jul. 15, 1988, Cambridge, Mass. US, pp. 199–207, XPOO2069634 see the whole document.
N. Rouas–Freiss et al. "The alpha1 domain of HLA–G1 and HLA–G2 inhibits cytotoxicity induced by natural killer cells: Is HLA–G the public ligand for natural killer cell inhibitory receptors?" Proceedings of the National Academy of Sciences, vol. 94, May 1, 1997, Washington DC. US, pp. 5249–5254, XP002046238 see the whole document.

* cited by examiner

Primary Examiner—Anne M. Wehbe'
(74) Attorney, Agent, or Firm—Oblon, Spivak, McClelland, Maier & Neustadt, P.C.

(57) ABSTRACT

The invention concerns the use of a eukaryotic cell coding for at least an HLA-G isoform, to obtain an immunomodulating medicine for inhibiting the activity of killer cells, in particular NK cells and/or for inhibiting the primary allogenic response, in parthologies or situations in which the killer cells are activated or for preparing a medicine to raise the inhibiting function of the isoform(s) expressed by said cells with respect to killer cells, in particular NK cells, in pathologies where these killer cells are inhibited by the molecule of the major histocompatibility complex of I HLA-G classes. The invention also concerns eukaryotic cells expressing at their surface at least an HLA-G isoform and their applications. The invention further concerns transgenic animals specifically expressing at least an HLA-G isoform.

7 Claims, 14 Drawing Sheets

Figure 1:
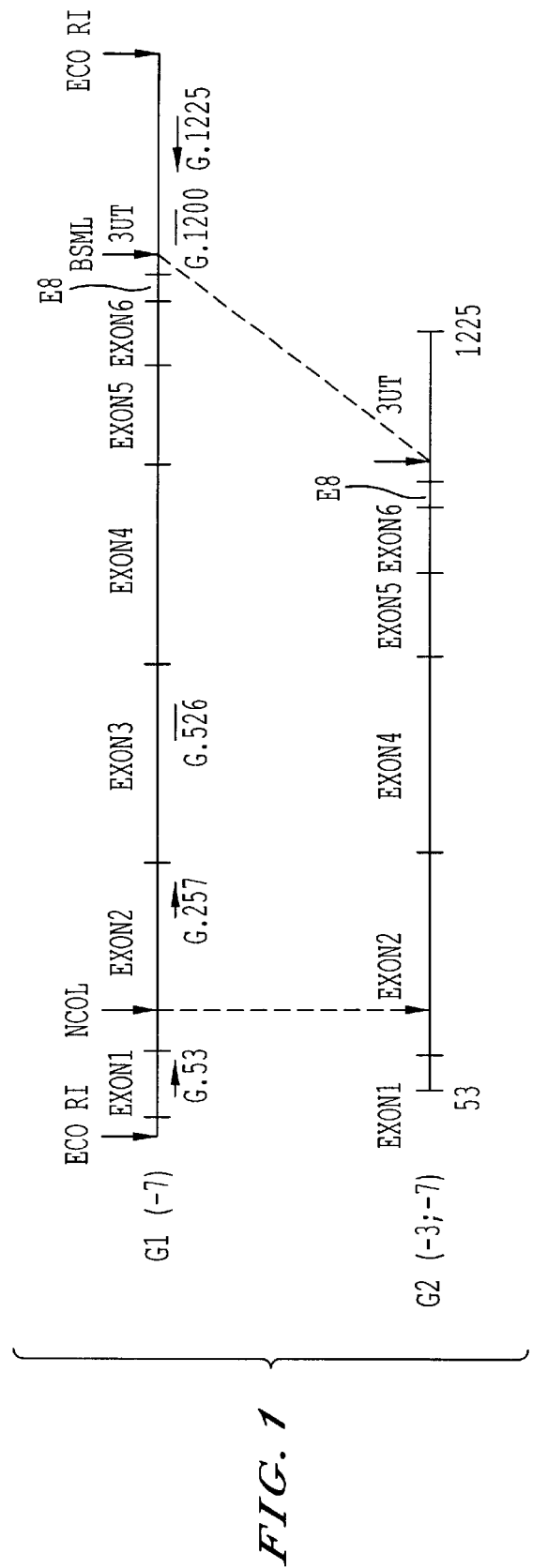

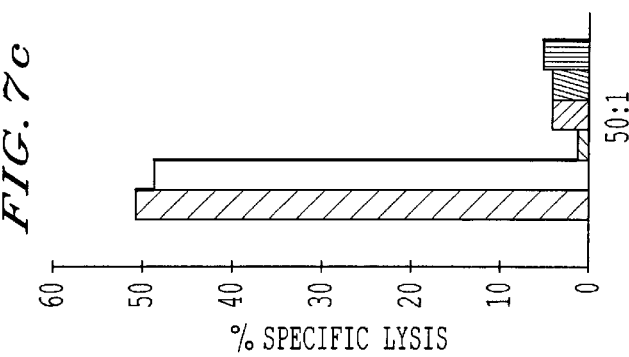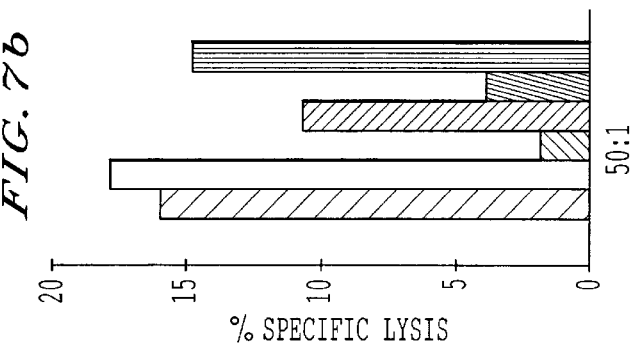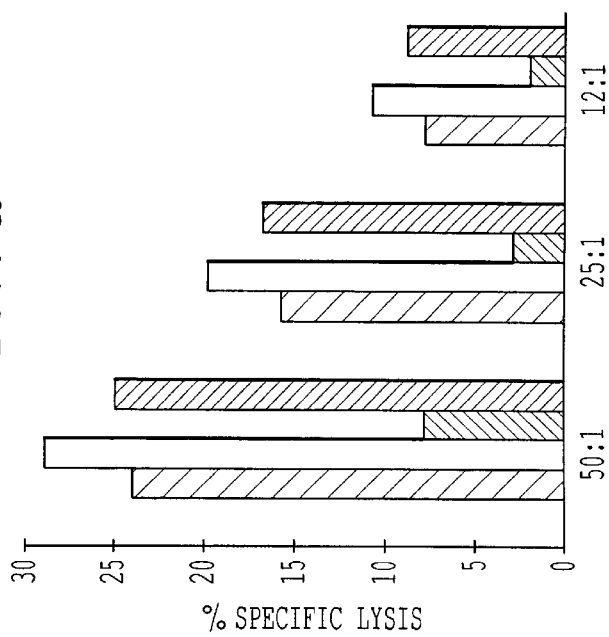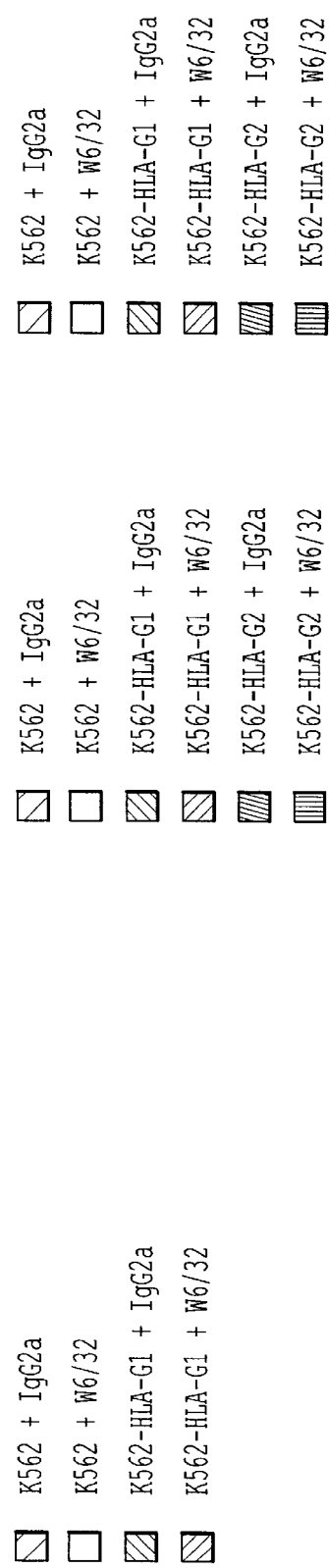
FIG. 7a, FIG. 7b, FIG. 7c

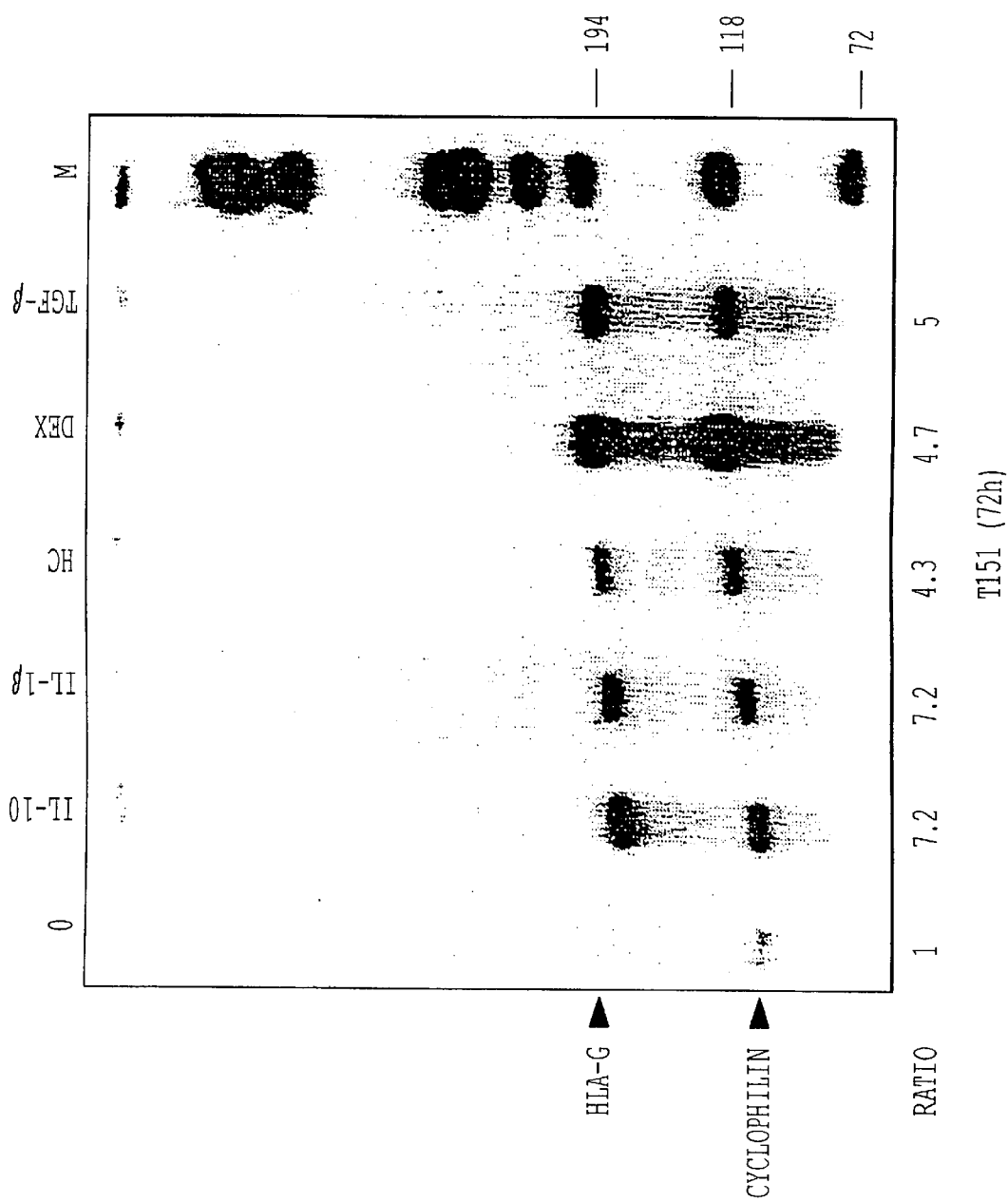

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic DNA

<400> SEQUENCE: 1
ccctttgtga cttcaagaac                                          20

<210> SEQ ID NO 2
<211> LENGTH: 48
<212> TYPE: DNA
<213> ORGANISM: Artificial Sequence
<220> FEATURE:
<223> OTHER INFORMATION: synthetic DNA

<400> SEQUENCE: 2
ggatcctaat acgactcact atagggaggt tatagctcag tggcccac           48

EUKARYOTIC CELLS EXPRESSING AT THEIR SURFACE AT LEAST AN HLA-G ISOFORM AND THEIR APPLICATIONS

The present invention relates to eukaryotic cells which express at least one HLA-G isoform on their surface and to their uses, in particular for obtaining a medicament for modulating the cytolytic activity of NK cells in pathologies in which these NK cells are activated or inhibited and as a model system for use, in particular, in a method for screening antineoplastic substances.

The present invention also relates to transgenic animals which specifically express at least one HLA-G isoform.

The antigens of the major histocompatibility complex (MHC) divide into several classes, i.e. class I antigens (HLA-A, HLA-B and HLA-C), which exhibit 3 globular domains ($\alpha 1$, $\alpha 2$ and $\alpha 3$) and whose $\alpha 3$ domain is associated with $\beta 2$ microglobulin, the class II antigens (HLA-DP, HLA-DQ and HLA-DR) and the class III antigens (complement).

In addition to the abovementioned antigens, the class I antigens include other antigens known as non-classical class I antigens, in particular the HLA-E, HLA-F and HLA-G antigens; this latter antigen, in particular, is expressed by the extravillous trophoblasts of the normal human placenta.

The sequence of the HLA-G gene (HLA-6.0 gene) has been described by Geraghty et al., (Proc. Natl. Acad. Sci. USA, 1987, 84, 9145–9149): it comprises 4396 base pairs and exhibits an intron/exon organization which is homologous with that of the HLA-A, -B and -C genes. More precisely, this gene comprises 8 exons, 7 introns and an untranslated 3' end; the 8 exons correspond, respectively, to: exon 1: signal sequence, exon 2: $\alpha 1$ extracellular domain, exon 3: $\alpha 2$ extracellular domain, exon 4: $\alpha 3$ extracellular domain, exon 5: transmembrane region, exon 6: cytoplasmic domain I, exon 7: cytoplasmic domain II (untranslated), exon 8: cytoplasmic domain III (untranslated) and untranslated 3' region (Geraghty et al., loc. cit.; Ellis et al., *J. Immunol.*, 1990, 144, 731–735; Kirszenbaum M. et al., *Oncogeny of hematopoiesis. Aplastic anemia* Eds. E. Gluckman, L. Coulombel, Inserm Symposium/John Libbey Eurotext Ltd). However, the HLA-G gene differs from the other class I genes in that the in-frame translation termination codon is located in the second codon of exon 6; as a consequence, the cytoplasmic region of the protein encoded by this HLA-6.0 gene is considerably shorter than that of the cytoplasmic regions of the HLA-A, -B and -C proteins.

These HLA-G antigens are mainly expressed by the cytotrophoblastic cells of the placenta and are regarded as playing a role in the protection of the foetus (no rejection by the mother). Furthermore, to the extent that the HLA-G gene is monomorphic, it may also be involved in the growth or function of the placental cells (Kovats et al., Science, 1990, 248, 220–223).

Other studies dealing with this non-classical class I antigen (Ishitani et al., Proc. Natl. Acad. Sci. USA, 1992, 89, 3947–3951) have shown that the primary transcript of the HLA-G gene can be spliced in several ways and produces at least 3 distinct mature mRNAs: the primary transcript of HLA-G gives one complete copy of 1200 bp (G1), one fragment of 900 bp (G2) and one fragment of 600 bp (G3).

The G1 transcript does not contain exon 7 and corresponds to the sequence described by Ellis et al. (loc. cit.), i.e. it encodes a protein which comprises a leader sequence, three external domains, a transmembrane region and a cytoplasmic sequence. The G2 mRNA does not contain exon 3, i.e. it encodes a protein in which the $\alpha 1$ and $\alpha 3$ domains are linked directly; the G3 mRNA contains neither exon 3 nor exon 4, i.e. it encodes a protein in which the $\alpha 1$ domain and the transmembrane sequence are linked directly.

The splicing which prevails for obtaining the HLA-G2 antigen entails an adenine (A) (originating from the domain encoding $\alpha 1$) being linked to an AC sequence (derived from the domain encoding $\alpha 3$), leading to the creation of an AAC (asparagine) codon in place of the GAC (aspartic acid) codon which is encountered at the beginning of the sequence which encodes the $\alpha 3$ domain in HLA-G1.

The splicing which is generated for obtaining HLA-G3 does not entail the formation of a new codon in the splicing zone.

The authors of this article have also analysed the different proteins which are expressed: the 3 mRNAs are translated into protein in the 0.221-G cell line.

The authors of this article conclude that HLA-G plays a fundamental role in protecting the foetus with regard to a maternal immune response (induction of immune tolerance). However, it is pointed out that the role of the G3 protein, which does not contain the $\alpha 3$ domain, is not established.

Some of the inventors have recently demonstrated the existence of other spliced forms of HLA-G mRNA: i.e. the HLA-G4 transcript, which does not include exon 4; the HLA-G5 transcript, which includes intron 4 between exons 4 and 5, thereby giving rise to a change in the reading frame during translation of this transcript, in particular to the appearance of a stop codon after amino acid 21 of intron 4; and the HLA-G6 transcript, which possesses intron 4 but which has lost exon 3 (Kirszenbaum M. et al., *Proc. Natl. Acad. Sci.* USA, 1994, 91, 4209–4213; European Application EP 0 677 582; Kirszenbaum M. et al., *Human Immunol.*, 1995, 43, 237–241; Moreau P. et al., *Human Immunol.*, 1995, 43, 231–236); they have also demonstrated that these different transcripts are expressed in several types of human foetal and adult cells, in particular in lymphocytes (Kirszenbaum M. et al., *Human Immunol.*, 1995, loc. cit.; Moreau P. et al., *Human Immunol.*, 1995, loc. cit.).

There are therefore at least 5 different HLA-G mRNAs which potentially encode 5 isoforms of HLA-G.

Although the foetus can be regarded as being a semiallograft, the foetal cells survive and are not rejected by the mother; it has emerged that the HLA-G molecules which are expressed on the surface of the trophoblasts protect the foetal cells from lysis by the maternal natural killer. (NK) cells (Carosella E. D. et al., C.R. Acad. Sci., 318, 827–830; Carosella E. D. et al., *Immunol. Today*, 1996, 407–409).

Earlier studies have demonstrated that expression of HLA-G molecules on the surface of target cells protects the said target cells from the lytic activity of the NK cells of the decidual layer of the maternal endometrium (Chumbley G. et al., *Cell Immunol.*, 1994, 155, 312–322; Deniz G. et al., *J. Immunol.*, 1994, 152, 4255–4261). It is to be noted that these target cells are obtained by means of transfection with vectors which contain the HLA-G genomic DNA, which is potentially able to generate all the alternative transcripts.

The NK cells express receptors for MHC class I molecules (killer inhibitory receptors or KIR or NKIR for NK inhibitory receptors), which receptors are responsible for inhibiting cytotoxicity when these HLA molecules, acting as ligands, are recognized by these receptors; for example, Pazmany L. et al., (Science, 1996, 274, 792–795) showed that the expression of HLA-G protected LCL 721.221 (B lymphoma cell line) target cells, which were transfected with the HLA-G gene, from lysis. These cells are ordinarily sensitive to NK cells; they furthermore identified the receptors on the NK cells which recognize HLA-G, namely the NKIR1 and NKIR2 receptors, which belong to the immunoglobulin (p58) superfamily and which are able to distinguish between two dimorphic groups of HLA-C molecules; HLA-G could be the natural ligand of the NK cell receptors; thus, some of the inventors have shown that NK cells do not express any HLA-G transcript; this result confirms that the expression products of the HLA-G gene probably play a role in immunotolerance (Teyssier M. et al., *Nat. Immunol.*, 1995, 14, 262–270).

In view of the important role which the HLA-G molecule may play both in pathologies in which the NK cells are particularly active (autoimmune diseases, transplantations) or in which they are, on the other hand, inhibited (abnormal presence of HLA-G molecules, in particular on certain tumours or in viral infections), the inventors surprisingly found, in continuing their studies, that it was possible to express one single isoform on the cell surface and to regulate its quantitative and qualitative expression and therefore to control its use.

The present invention relates to eukaryotic cells which are obtained by genetic modification, characterized in that they are transfected with an expression vector which contains at least one cDNA encoding an HLA-G isoform which is selected from the group consisting of the HLA-G2, HLA-G3, HLA-G4, HLA-G5 and HLA-G6 isoforms.

The present invention also relates to eukaryotic cells which are obtained by genetic modification, characterized in that they are transfected with an expression vector which contains a suitable origin of replication, a selection marker such as a gene for resistance to an antibiotic, the RSV viral promoter and a cDNA which encodes an HLA-G isoform which is selected from the group consisting of the HLA-G1, HLA-G2, HLA-G3, HLA-G4, HLA-G5 and HLA-G6 isoforms.

These cells efficiently express the different isoforms in a glycosylated form which is similar to that encountered under biological conditions.

According to one advantageous embodiment of the said transfected eukaryotic cells, the said cDNA encodes an isoform which contains at least one extracellular domain, in particular the $\alpha 1$ domain.

Surprisingly, the cytolytic activity of the NK cells is inhibited in the presence of the said eukaryotic cells which have been transfected in this way irrespective of the isoform expressed (membrane isoform or secreted isoform).

The said eukaryotic cells may be derived from any animal and may in particular be mammalian cells, more especially human cells.

Both the transfected cells according to the invention and eukaryotic cells which are transfected with a vector expressing the HLA-G1 isoform can be used:

in order to obtain an immunomodulatory medicament for inhibiting the activity of killer cells, in particular NK cells and/or for inhibiting the primary allogeneic response; an immunomodulatory product which has a general action or an immunomodulatory product which has a specific action, and which is in particular suitable for protecting a transplanted organ, is obtained depending on the type of eukaryotic cells transfected; transfected haematopoietic stem cells, hepatic cells and renal cells may be mentioned as non-limiting examples; unexpectedly, the said eukaryotic cells protect the target cells from attack by all classes of NK cells irrespective of the HLA-G isoform expressed; these eukaryotic cells are particularly suitable for use in the prevention of graft rejection (allografts and xenografts), in the prevention of repeat abortions and in the treatment of autoimmune diseases and pathologies or situations in which killer cells are activated in a general manner;

in order to obtain a medicament for relieving the inhibitory function of the isoform(s) expressed by the said cells with regard to killer cells, in particular NK cells, in pathologies in which these killer cells are inhibited by the HLA-G class I major histocompatibility complex molecule; thus, solid tumours express some HLA-G isoforms; this expression protects these cancerous cells from the lysis which is induced by NK cells;

in order to produce antineoplastic vaccines: production of antibodies which block the HLA-G antigen and thereby reinduce the activity of the NK cells;

in order to produce human cells which are capable of being transplanted into a specific organ and of protecting this latter organ from the lysis which is induced by killer cells, in particular NK cells;

as a model for studying the interaction of HLA-G and immunocompetent cells, in particular killer cells, more especially NK cells, in order to find effectors which are capable of modulating the antineoplastic response and inhibiting the HLA-G expression which is induced in some cancers while at the same retaining the expression of the classic HLA antigens; this enables them to be used for obtaining a medicament for relieving the inhibitory function of the isoform(s) expressed by the said cells with regard to killer cells, in particular NK cells, in pathologies, such as cancers, in which these NK cells are inhibited by the HLA-G class I major histocompatibility complex molecule;

in order to produce non-human transgenic mammals which express a specific HLA-G isoform and which are able to produce tissues which express the said isoform (xenograft donors) and/or which are able to form models for studying the regulation and the function of the different tolerance-linked HLA-G isoforms in autoimmune diseases and during transplanting.

In order to produce the said transgenic animals, in particular transgenic mice, at least one copy of a segment containing a cDNA which encodes an HLA-G isoform linked to a suitable promoter is introduced into the cells of a mouse embryo at an early stage.

The present invention also relates to a purified and isolated receptor, characterized in that the receptor is capable of binding at least one HLA-G isoform which is expressed on the surface of a eukaryotic target cell such as defined above, in that the said receptor is expressed on the surface of T cell lines which neither express any CD94, KIR1 or KIR2 inhibitory receptor nor at least some membrane receptors which are specific for T cells, and in that the formation of the HLA-G isoform/receptor complex inhibits the lysis of the target cells by the said T cell lines.

Advantageously, the said T cell lines do not express at least the CD3 and $\alpha\beta$ receptors or do not express any membrane receptor which is specific for T cells.

The immature leukaemic T cell line designated YT2C2 is a cell line of this type since it does not express any CD94, KIR1 or KIR2 inhibitory receptor nor receptors which are specific for T cells, such as the CD3 and $\alpha\beta$ receptors.

In order to isolate the said receptor, it is possible:

a) either to incubate the said T cell lines with an HLA-G isoform, in particular with the soluble HLA-G5 isoform, isolate the resulting HLA-G/receptor complex by treating cell lines with trypsin, dissociate the receptor from the HLA-G molecule by treating with a denaturing agent such as a detergent, and separate the receptor, either by passing the resulting mixture through an immunoaffinity column coupled to an anti-HLA-G antibody and recovering the free receptor in the eluate, or by subjecting the said mixture to a suitable electrophoresis.

b) or to clone the said receptor in accordance with the method described in Colonna M. et al., Science, 1995, 268, 405–408.

The present invention also relates to a process for studying the binding affinity of an HLA-G isoform for a KIR receptor or a receptor such as defined above (receptor having NK activity), characterized in that the process comprises:

transfecting a eukaryotic host cell with an expression vector containing a cDNA encoding an HLA-G isoform, culturing the said host cells such that they express the said HLA-G isoform on their surface, bringing the said transfected eukaryotic cells into contact with killer cells, such as the NK cells or the T cell lines as defined above, in the presence of substances which activate or inhibit the HLA-G and/or substances which activate or inhibit the KIR receptor or the receptor having NK activity in accordance with the invention and measuring the quantity of HLA-G isoform/receptor complex.

The present invention also relates to products which comprise a eukaryotic cell expressing at least one HLA-G isoform as defined above and a factor for stimulating the expression of HLA-Gs, as combination products for simultaneous or separate use or use which is staggered over time, in the prevention or treatment of pathologies or situations in which the killer cells are activated, such as transplants, repeat abortions or autoimmune diseases.

In accordance with the invention, the said stimulatory factor is selected from the group consisting of corticoids and cytokines.

In addition to the above provisions, the invention also comprises other provisions which will emerge from the description which follows and which refers to examples of embodiments of the present invention and to the attached drawings in which:

FIG. 1 illustrates the construction of the HLA-G2 cDNA fragment. The vertical arrows indicate the sites of restriction enzymes which are specific for producing the HLA-G2 cDNA from the HLA-G1 cDNA. The horizontal arrows indicate the PCR primers (G.53, G.257 and G.1225) and the horizontal lines without arrows indicate the specific HLA-G probes used for the hybridization (G.526 and G.1200).

Figure 2:
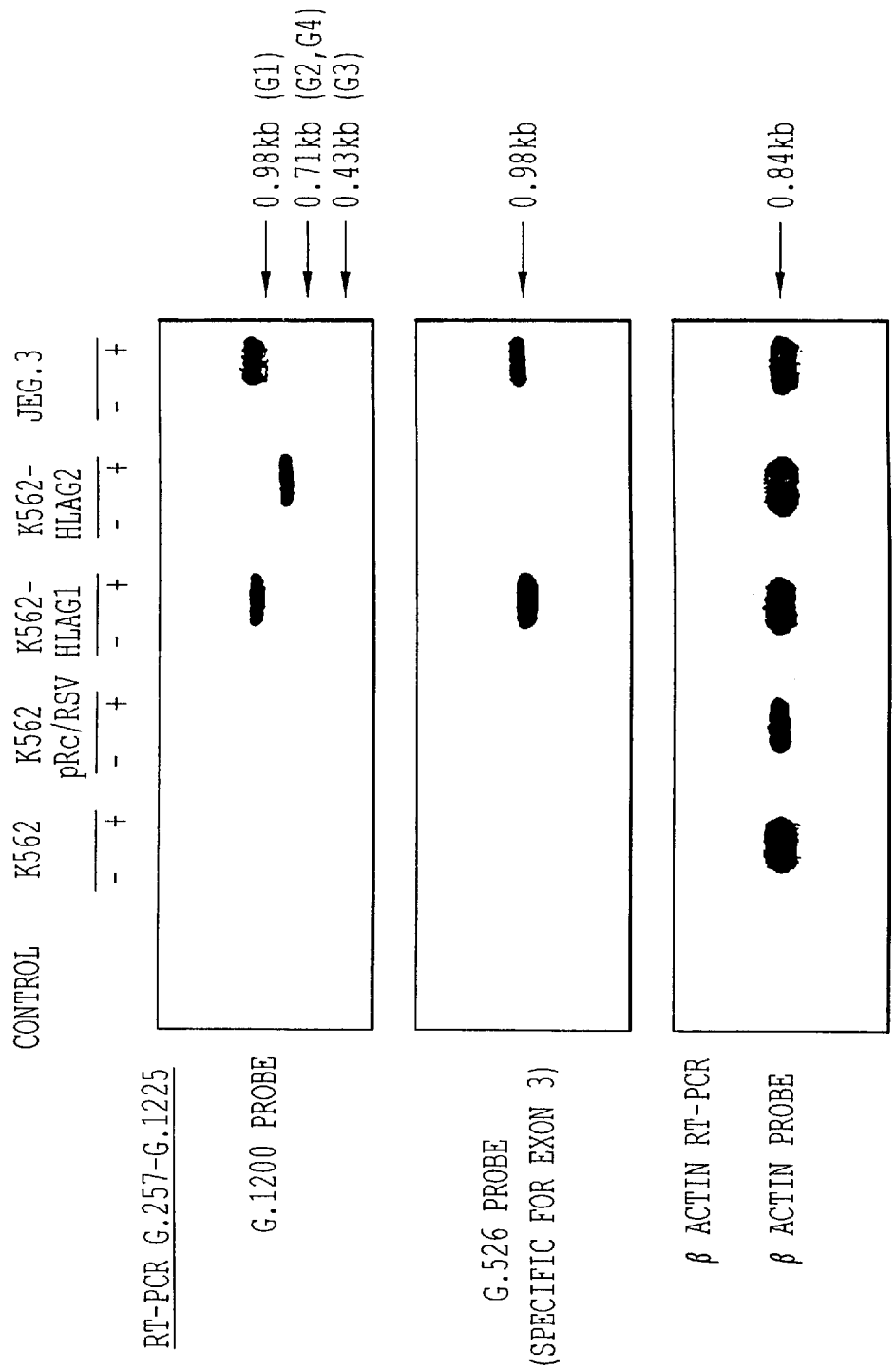

FIG. 2 illustrates the detection of the HLA-G transcripts in the parental cell line K562, the transfectants according to the invention and the cell line JEG-3. The RNAs are amplified using the specific HLA-G primers G.257 and G.1225; the Southern blot is obtained by hybridizing with $^{32}$phosphorus-labelled probes G.1200 or G.526. The positive (+) and negative (−) lanes correspond to the RT$^+$ and RT$^-$ templates and the blank is a control which is carried out using a PCR mixture without any cDNA template. In order to check the quantity of RNA in each sample, the results of the PCR amplification obtained with primers which are specific for β-actin and a Southern blot are hybridized with a β-actin probe labelled with $^-$p phosphorus.

Figure 3:
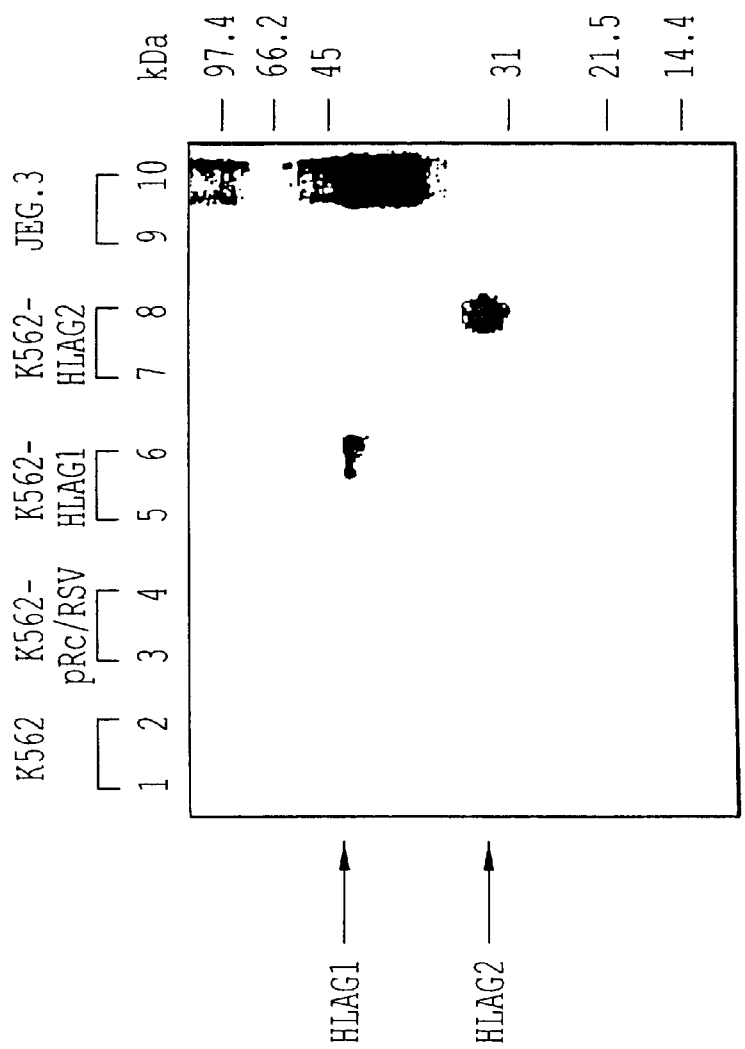
Figure 4A:
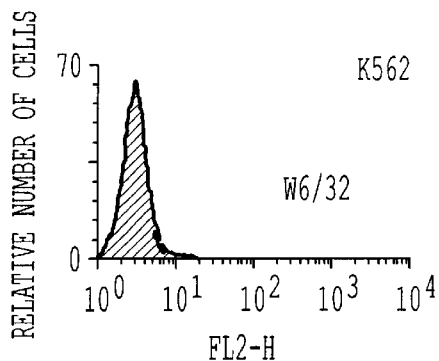
Figure 4B:
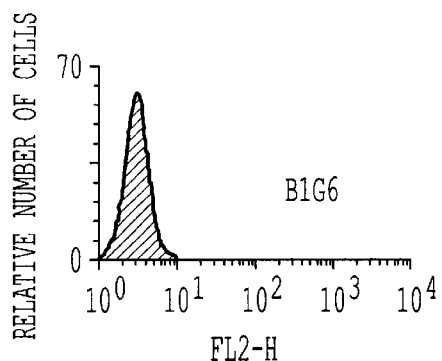
Figure 4C:
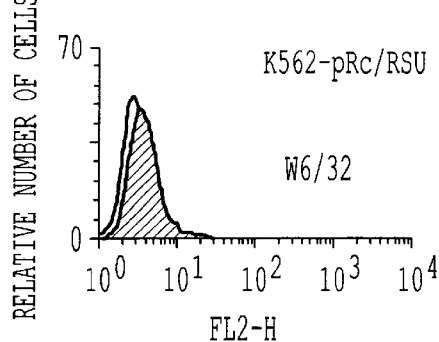
Figure 4D:
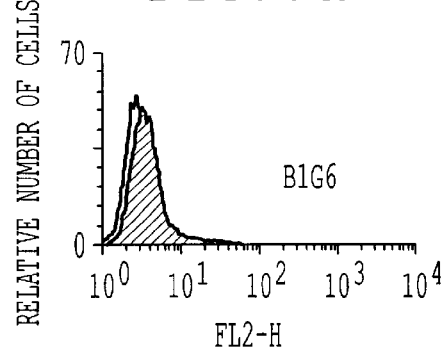
Figure 4E:
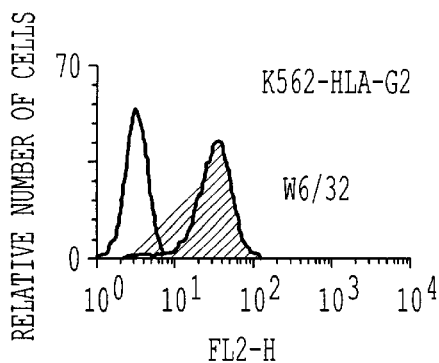
Figure 4F:
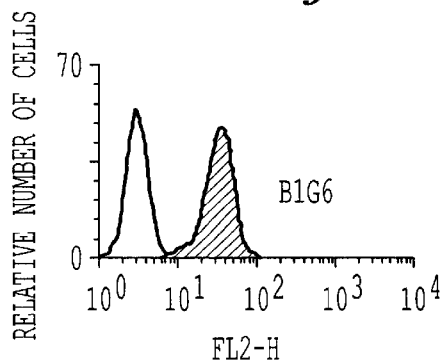
Figure 4G:
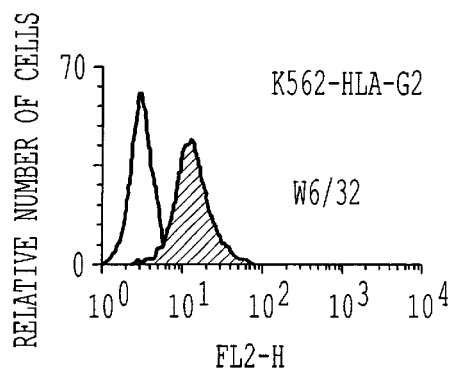
Figure 4H:
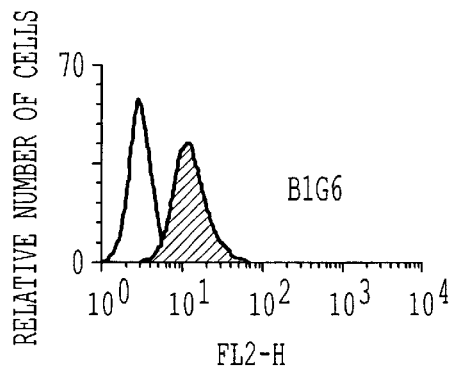
Figure 4I:
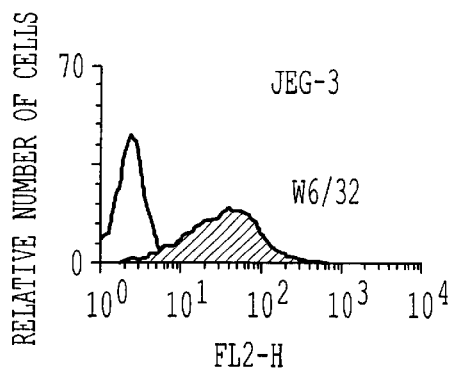
Figure 4J:
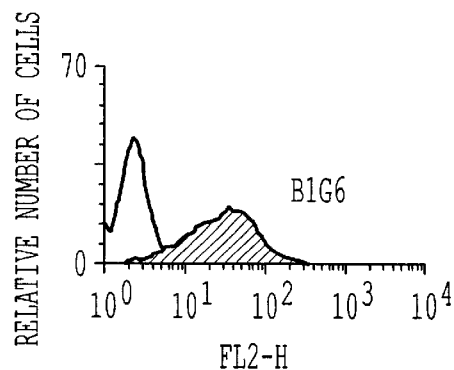

FIG. 3 illustrates the immunoprecipitation, the SDS-PAGE and the Western blot analysis of the biotin-labelled cell surface proteins. Biotinylated membrane lysates of K562 cells (lanes 1 and 2), K562-pRc/RSV cells (lanes 3 and 4), K562-HLA-G1 cells (lanes 5 and 6), K562-HLA-G2 cells (lanes 7 and 8) and JEG-3 cells (lanes 9 and 10) are immunoprecipitated with a control monoclonal antibody UHC-10 (lanes 1, 3, 5, 7 and 9) or a monoclonal antibody W6/32 (lanes 2, 4, 6, 8 and 10) and analysed by 10% SDS-PAGE under reducing conditions. The molecular weight markers are indicated on the right.

FIG. 4 illustrates the expression of the HLA molecules on the transfectants of the K562 cell line, as detected by cytofluorimetry. The wild-type K562 cells, the K562 cells which are transfected either with the vector alone (K562 pRc/RSV) or with the vectors containing the cDNA encoding HLA-G1 (K562-HLA-G1) or the cDNA encoding HLA-G2 (K562-HLA-G2) and the JEG-3 cells are labelled by indirect immunofluoresence with the following primary monoclonal antibodies (profiles in bold): monomorphic anti-class I antibody W6/32 (left-hand part of the figure) and anti-human β2 m antibody B1.G6 (right-hand part of the figure). Controls are carried out on the same cells labelled with a control antibody (profiles in white). After washing, the cells are labelled with an F(ab)'2 antibody from goat anti-mouse IgG immunoglobulin conjugated to phycoerythrin. The results were repeated at least five times.

Figure 5C:
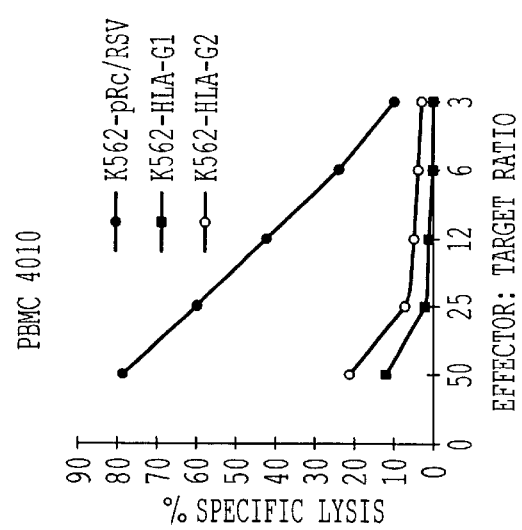
Figure 5B:
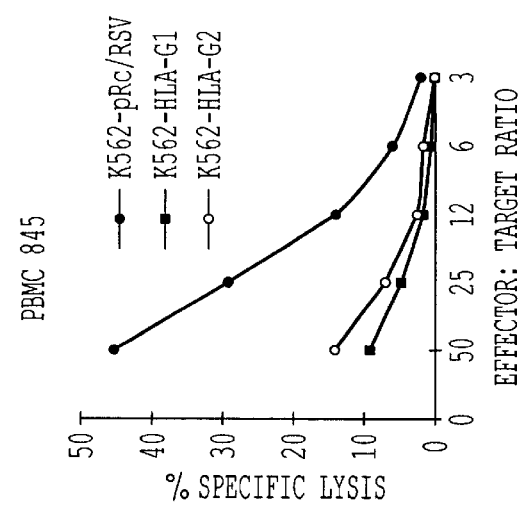
Figure 5A:
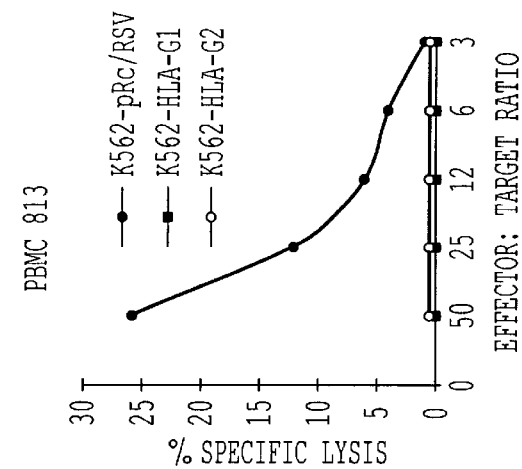

FIGS. 5(A–C) illustrates the effect of the expression of HLA-G1 and HLA-G2 molecules on the lytic activity of NK cells. K562 cells which are transfected either with the vector alone or with the HLA-G1 vector or the HLA-G2 vector are used as targets (T). Peripheral blood mononuclear cells (PBMC) which have been freshly isolated from the following different donors: (A) donor 4010 (HLA-A3, -B44, -B56 and -Cw1), (B) donor 845 (HLA-A1, -A28, -B8, -B51 and -Cw7) and (C) donor 813 (HLA-A2, -B27, -B51 and -Cw1) are used as effector cells (E). The results are expressed as the percentage lysis which is recorded over 4 hours in a chromium 51 ($^{51}$Cr) liberation test. The standard deviation of the mean of triplicates is below 5% and the spontaneous liberation never exceeds 10% of the maximum liberation.

Figure 6:
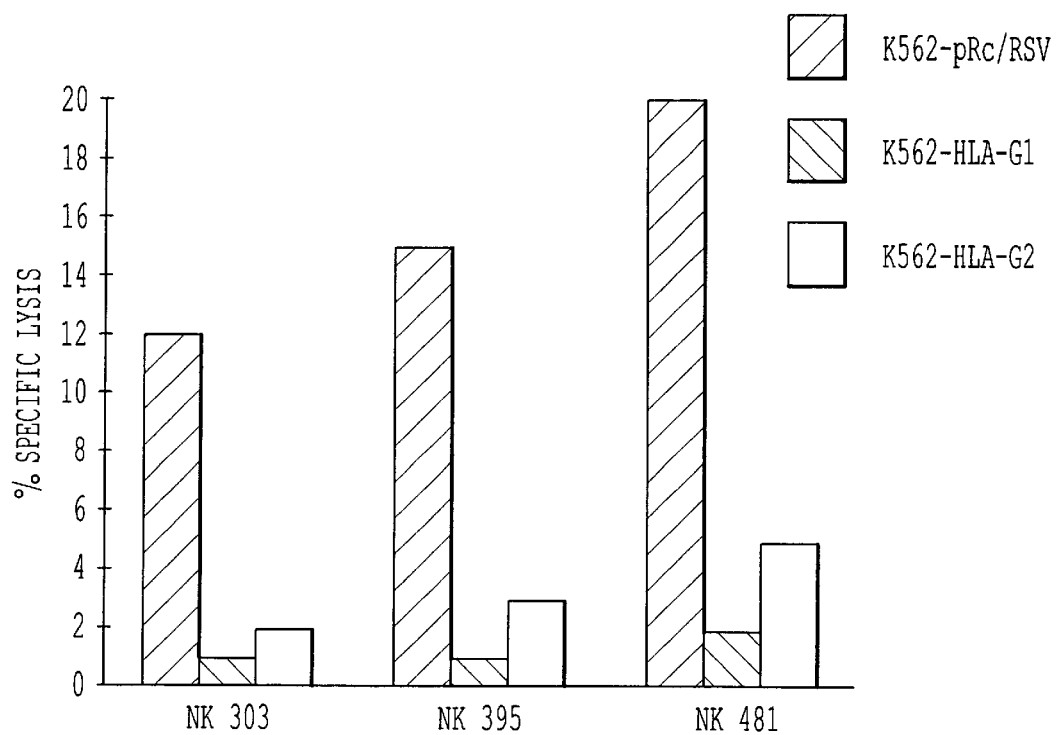

FIG. 6 illustrates the effect of the expression of HLA-G1 and HLA-G2 molecules on the lysis which is induced by polyclonal NK cells. K562 cells which are transfected either with the vector alone, with the HLA-G1 vector or with the HLA-G2 vector are used as targets (T) for the NK cells (more than 95% of which have the following phenotype: CD3−, CD16+ and CD56+) isolated from the donor designated 303 (HLA-A29, -B44, -B62 and -Cw3, -Cw5) in an E:T ratio of 1:1, from the donor designated 395 (HLA-A2, -B13, -B44 and -Cw1) in an E:T ratio of 1:1 and from the donor 481 (HLA-A3, -A26, -B27, -B35, and -Cw4, -Cw2) in an E:T ratio of 5:1. These results are expressed as the percentage lysis which is recorded over 4 hours in a $^{51}$Cr liberation test. The standard deviation of the mean of triplicates is below 5% and the spontaneous liberation never exceeds 10% of the maximum liberation.

FIGS. 7(A–C) illustrates the effect of a treatment with a monoclonal antibody on the resistance of target cells which have been transfected with an HLA-G1 or HLA-G2 vector to lysis induced by NK cells. The cytotoxicity is set up using the indicated targets and (A) peripheral blood mononuclear cells from donor 382 (HLA-A11, -A29, -B44 and -Cw5), (B) peripheral blood mononuclear cells from donor 845 (HLA-A1, -A28, -B8, -B51 and -Cw7) and (C) clone YT2C2 as effector cells (E). W6/32 or IgG2a-type control antibodies are added to the assay at a concentration of 10 μg/ml. The toxicities of the monoclonal antibodies are checked for each test and are always less than 3%.

Figure 8:
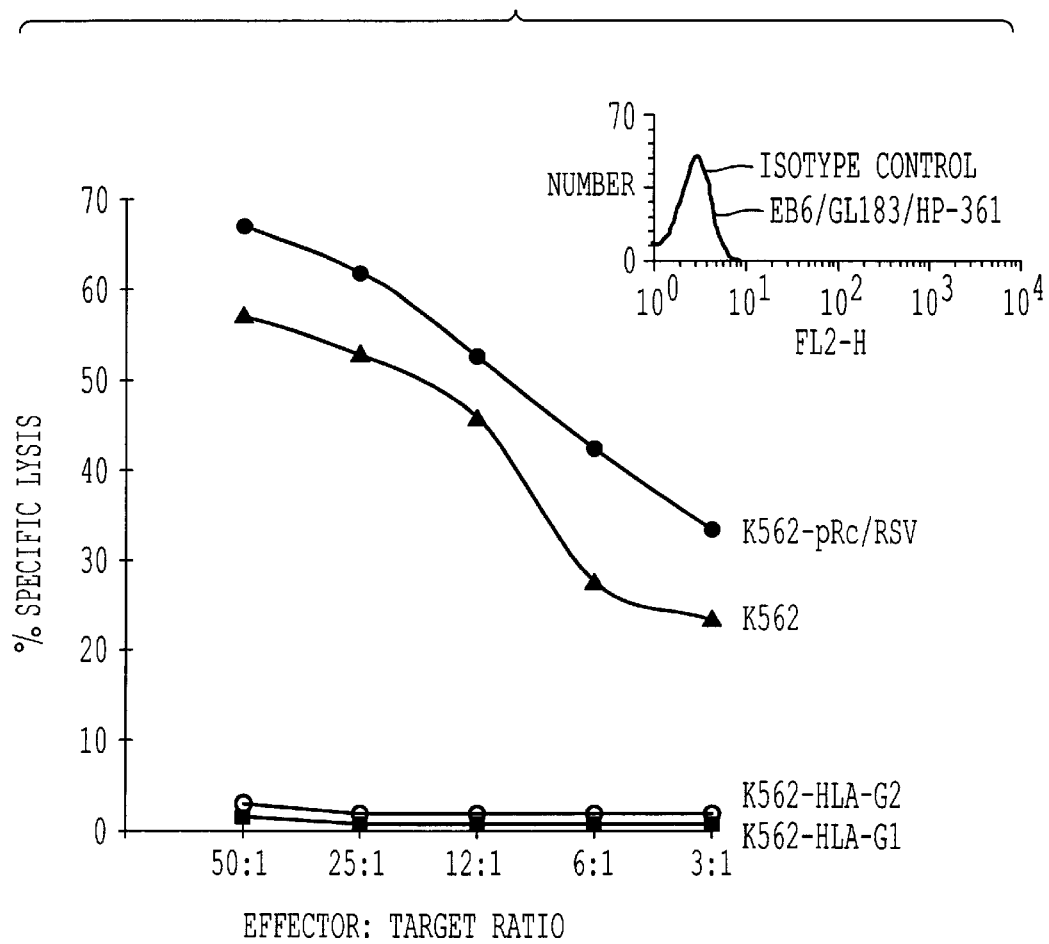

FIG. 8 illustrates the effect of HLA-G1 and HLA-G2 expression on the sensitivity of the cytotoxicity of clone YT2C2. K562 cells transfected either with the vector alone, or with the HLA-G1 vector or the HLA-G2 vector are used as target cells (T). The results are expressed as the percentage lysis which is recorded over 4 hours in a chromium 51 liberation test. The standard deviation of the mean of triplicates is less than 5% and the spontaneous liberation never exceeds 10% of the maximum liberation. This experiment was repeated at least 5 times and produced the same results on each occasion. Expression of NKIR receptors on the YT2C2 clone was demonstrated by cytofluorimetry. The YT2C2 cells are labelled by indirect immunofluorescence using the following primary monoclonal antibodies: EB6 (IgG1, anti-p58.1 or NKIR1), GL183 (IgG1, anti-p58.2 or NKIR2) and HP-3B1 (IgG2a, anti-CD94). The controls are the same cells labelled with an irrelevant antibody. After washing, the cells are labelled with an F(ab)'2 from goat anti-mouse IgG antibody/phycoerythrin conjugate. Only one of the four assays is shown in this figure.

Figure 9:
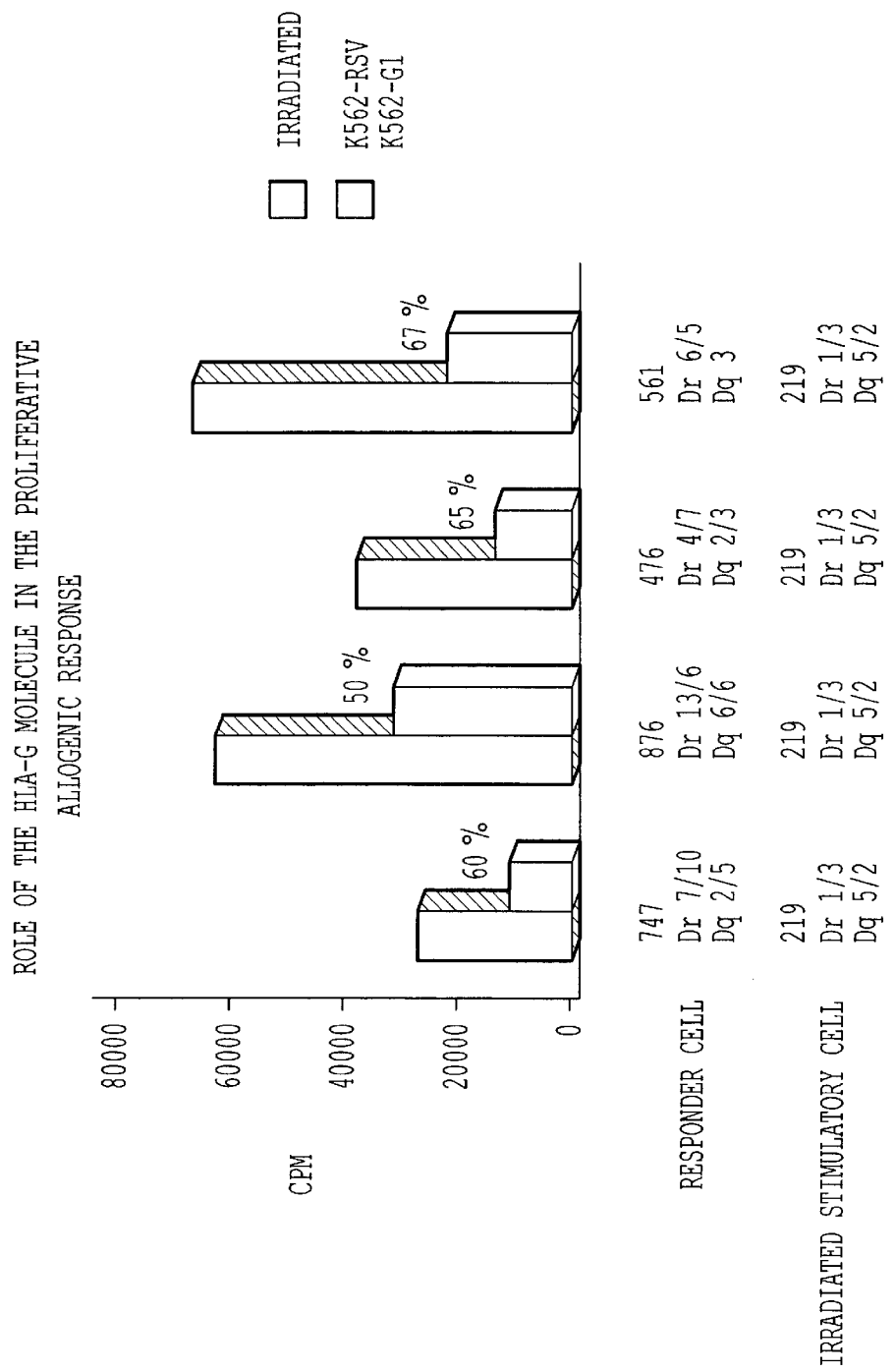

FIG. 9 illustrates the inhibitory activity of HLA-G isoforms in the proliferative allogeneic response.

Figure 10:
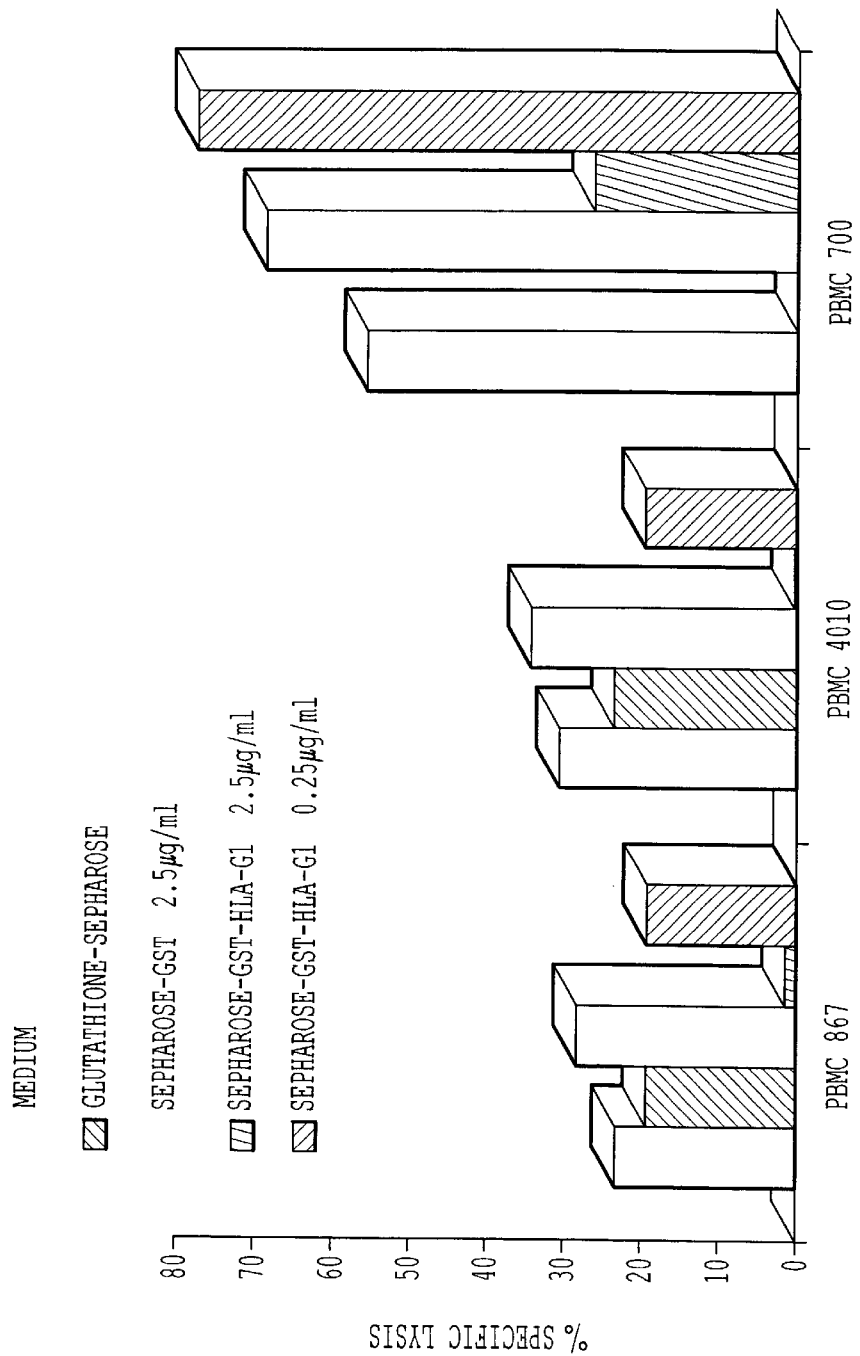
Figure 11:
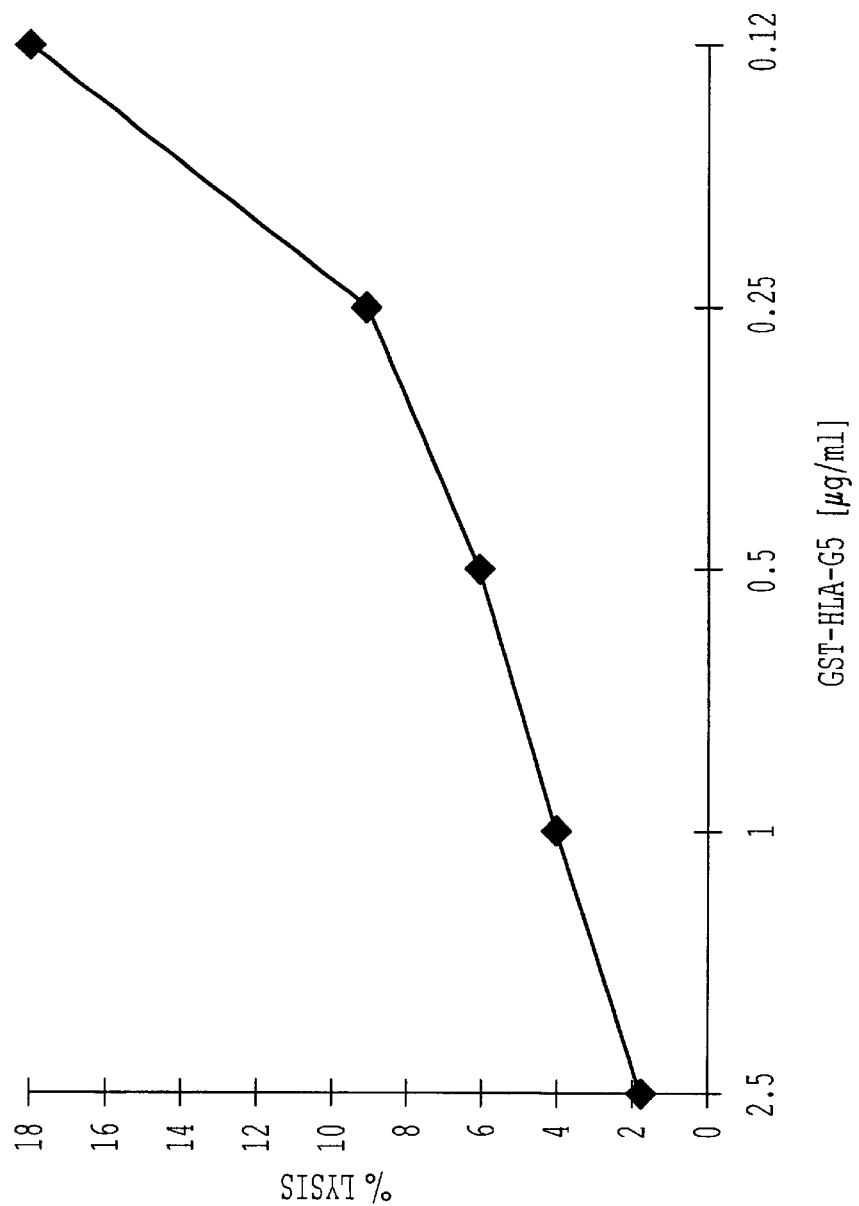

FIGS. 10 and 11 illustrate inhibition of NK activity by the HLA-G5 isoform which is in the form of a fusion protein together with glutathione S-transferase (GST-HLA-G5). In FIG. 10, beads of Sepharose-GST-HLA-G5 are used at an estimated initial concentration of 25 mg/ml in a 1×PBS buffer. The control media are supplemented with 1×PBS in order to replace the sample. Peripheral blood mononuclear cells from donor 867 (HLA-A2, -A30, -B13, -B27 and Cw6), from donor 4010 (HLA-A3, -B44, -B56 and Cw1) and from donor 700 (HLA-A1, -A30, -B8, -B13 and Cw7) are used as effector cells (E). K562 cells are used as target cells (T). The E:T ratio is 50. The results are expressed, as specified above, in percentage lysis which is recorded over 4 hours in a chromium 51 ($^{51}$Cr) liberation test.

Figures 13A, 13B:
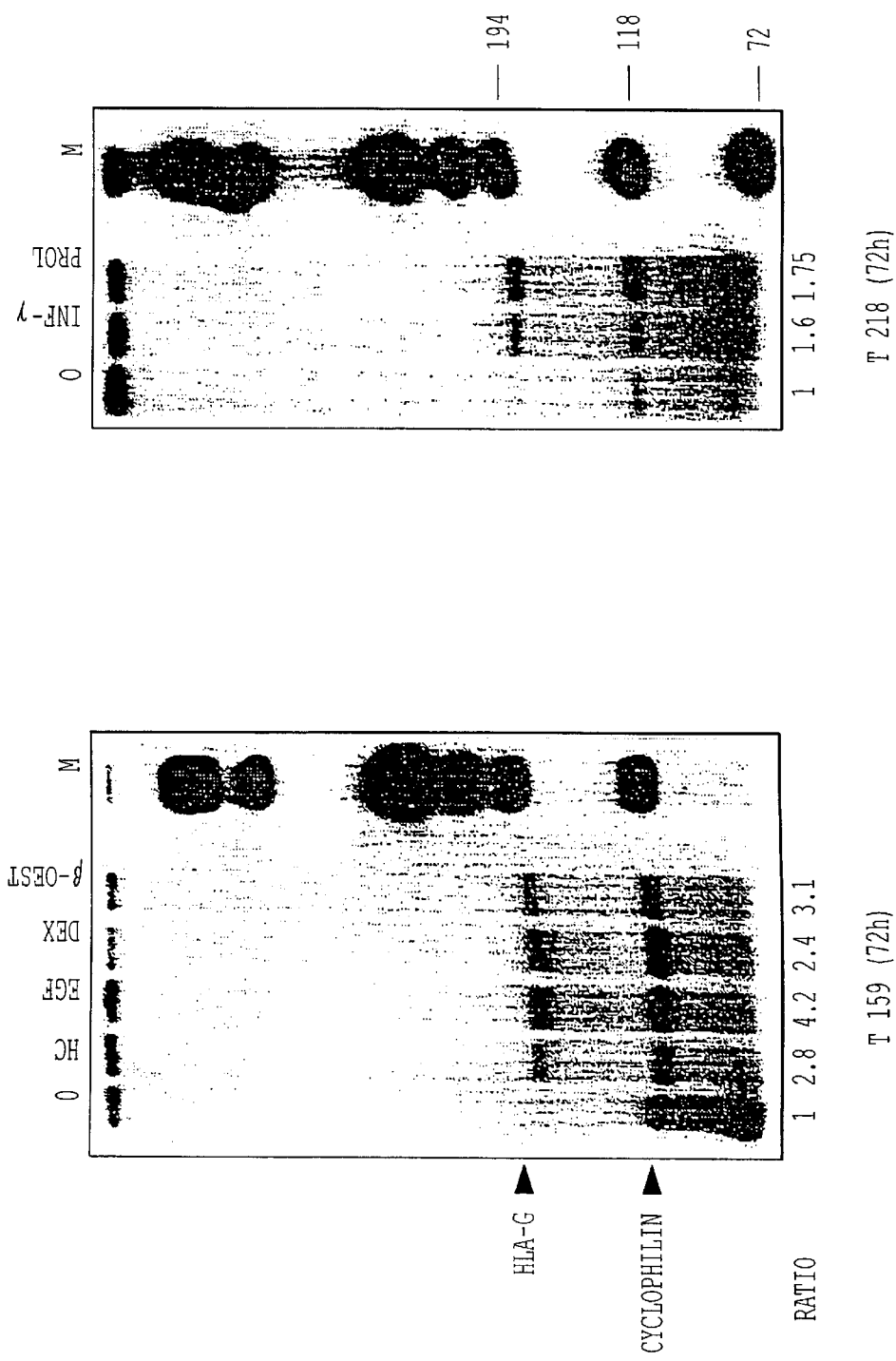

FIGS. 12 and 13 illustrate the increase which occurs in the transcription of the HLA-Gs in the presence of glucocorticoids or cytokines.

It should be fully understood, however, that these examples are given solely by way of illustrating the subject-matter of the invention, to which they in no way constitute a limitation.

EXAMPLE 1

Production of Cell Lines Containing the HLA-G transfectants; Their Role in Protecting Cells which Express These Molecules on Their Surface Against the Cytotoxicity of NK Cells

A/MATERIALS AND METHODS

1/Cell lines:

The human erythroleukaemic cell line K562 (ATCC) and the immature leukaemic T cell line (clone YT2C2 having NK activity) are maintained in an RPMI 1640 medium, which is supplemented with heat-inactivated 10% foetal calf serum, 2 mM L-glutamine, 1 μg/ml gentamicin and fungizone (Sigma, Saint-Quentin, France), and cultured at 37° C. in an incubator containing a humidified atmosphere which is 5%-enriched in $CO_2$. The K562 transfectants are selected in a medium containing 1 mg/ml geneticin (G418 sulphate, Sigma).

The human choriocarcinoma HLA-G-positive cell line designated JEG-3 (ATCC) is cultured in a DMEM medium (Sigma) which is supplemented with 10% heat-inactivated foetal calf serum, antibiotics and 2 mM L-glutamine. The cell lines do not contain any mycoplasmas.

2/The HLA-G vectors:

In order to obtain the HLA-G1 and HLA-G2 transfectants, the corresponding cDNAs are inserted into a eukaryotic expression vector which is designated pRc/RSV (Invitrogen, San Diego, Calif.) and which contains the Rous sarcoma virus (RSV) as the promoter and the neomycin gene as the selection marker. The general strategy for constructing the vector is shown in FIG. 1.

Briefly, the EcoRI fragment of the cDNA encoding HLA-G1, of 1.5 kb in length, is cut to produce blunt ends using a Klenow fragment of DNA polymerase I and fused with vector pRc/RSV which has been digested with the enzyme HindIII and dephosphorylated with calf intestinal phosphatase (GIBCO-BRL, Life Technologies, Eragny, France). The correct orientation of this construct, designated pRc/RSV-G1, is confirmed by enzymic digestion and sequencing.

In order to obtain recombinant plasmids containing the sequence encoding HLA-G2, the EcoR1 fragment of the cDNA encoding the HLA-G1 molecule is inserted into the EcoRI site of the vector pGEX-4T-3 (Pharmacia Biotech., Orsay, France). The cDNA fragment encoding the HLA-G2 molecule is obtained by means of PCR amplification as described in Kirszenbaum M. et al., Proc. Natl. Acad. Sci. USA, 1994, 91, 4209–4213, using the HLA-G-specific primers G.53 and G.1225. The resulting fragment is then digested with the restriction enzymes NcoI/BsmI and inserted into vector pGEX-HLA-G1 from which the NcoI/BsmI fragment containing the region encoding the α2 domain has previously been removed (pGEX-HLA-G2). The plasmid for expressing HLA-G2, designated pRc/RSV-G2, is obtained after EcoRI digestion of vector pGEX-HLA-G2; the CDNA fragment is cut to give blunt ends and inserted into vector pRc/RSV which has been digested with the restriction enzyme HindIII, and which has been previously cut, to give blunt ends, and dephosphorylated.

Vectors containing the HLA-G3, HLA-G4, HLA-G5 and HLA-G6 isoforms can be prepared in an identical manner; the sequences encoding these different isoforms were described in European Patent Application No. 0 677 582.

3/Cell lines harbouring the HLA-G transfectants:

Vectors containing the pRc/RSV-G1 sequence or the pRc/RSV-G2 sequence, as well as the pRc/RSV vector which serves as a control, are transfected into K562 cells by means of electroporation (Bio-Rad Gene Pulsar at 250 V and 960 μF). After two days of culturing, the cells are selected with 1 mg/ml geneticin in an RPMI medium containing 10% foetal calf serum. The cells harbouring the transfectants are checked by flow cytometry analysis so as to confirm expression of the HLA class I molecules.

In order to obtain a high level of expression of HLA-G in the K562 transfectants, the cells are isolated by cell sorting after immunolabelling (fluorescence-activated cell sorting or FACS, Vantage-Becton Dickinson, Pont de Claix, France) using a monoclonal antibody which is specific for class I HLAs.

4/RT-PCT analyses:

The total mRNA is extracted from $10^7$ cells using the RNA NOW reagent (Biogentex, Inc.) in accordance with the manufacturer's recommendations. The quality of the RNA is checked by electrophoresis in a 1.5% denaturing agarose gel. The cDNAs are prepared from 10 μg of DNAse I (Boerhinger Mannheim)-treated total RNA using an oligo-$(dT)_{12-18}$ primer and M-MLV reverse transcriptase (GIBCO-BRL). The RT-PCR amplifications are carried out using two HLA-G specific primers, i.e. G.257 (exon 2) and G.1225 (3'-UT), as described in Kirszenbaum M. et al. (1994) (loc. cit.). An RT reaction mixture without M-MLV reverse transcriptase (RT⁻) and a PCR mixture without cDNA template (blank) are used as controls in all the PCR amplifications. An additional RT-PCR amplification of β-actin is carried out in order to be able to check the quantity of RNA in all the samples. The PCR products are analysed by electrophoresis in a 1% agarose gel and stained with ethidium bromide. The specificity of the PCR products is confirmed by alkaline blotting of the fragments, in 0.4 N NaOH, onto nylon membranes (Hybond N+, Amersham, France). Hybridization is carried out using the probes G.1200 and G.526 (specific for exon 3) as described in Kirszenbaum M. et al., 1994 (loc. cit.). The filters are exposed to Kodak (Biomax) films, using intensifying screens, at −80° C. for from 4 to 16 hours.

5/Immunoprecipitation and SDS-PAGE electrophoresis:

The JEG-3 and K562 cell lines and the transfectant cell lines are surface-labelled with biotin (Interchim) and then washed and solubilized in a lysis buffer containing 1% Triton X100, 50 mM Tris-HC1, pH 7.4, 1 mM EDTA, 150 mM NaCl, 1 mM phenylmethylsulphonyl fluoride, 10 μg/ml aprotinin and 10 μg/ml leupeptin (Sigma, Saint-Quentin, France). The lysates are centrifuged at 13,000 rpm and preclarified by incubating with a Sepharose-protein A CL-4B (Pharmacia Biotechnology, Inc., Upsala, Sweden) column. The preclarified cell lysates are divided into two samples, to each of which are added Sepharose-protein A beads which have been previously incubated either with a mouse monoclonal antibody, W6/32, which is directed against class I antigens or a control monoclonal antibody (UPC-10, mouse IgG2a, Sigma). Following a two hour incubation at 4° C., the beads carrying the immune complexes are washed and treated with an SDS buffer; the bound antigen is eluted by boiling the beads. The precipitated proteins are analysed by 10% SDS-PAGE electrophoresis. The gels are transferred onto nitrocellulose filters, blocked in a PBS/0.2% Tween 20/5% bovine serum albumin (BSA) buffer (incubated overnight at 4° C.) and washed in a PBS/Tween buffer. The filters are then incubated for 40 minutes at ambient temperature with a horse radish peroxidase-streptavidin conjugate. After the membrane has been washed extensively, the colouring reaction is carried out using the Western blotting detection reagent ECL (Amersham, France), after which the membrane is exposed to a Kodak film at ambient temperature.

6/Monoclonal antibodies and flow cytometry analyses:

The following antibodies are employed: W6/32: IgG2a, anti-HLA class I α chains which are associated with β2-m (Sigma); B1G6: IgG2a, anti-β2-m (Sigma); GL183: IgG1, anti-p58 (Immunotech, Marseille, France); EB6: IgG1, anti-p58 (Immunotech); HP-3B1: IgG2a, anti-CD94 (Immunotech); UCHT-1: IgG1, quantum red-conjugated anti-CD3 (Sigma); 3G8: IgG1, fluorescein-conjugated anti-CD16 (Immunotech); and B 159: IgG1 phycoerythrin-conjugated anti-CD56 (Immunotech).

For the flow cytometry assays, the cells are washed in a PBS buffer and labelled, at 4° C. for 30 minutes, with the corresponding monoclonal antibody in PBS/1% bovine serum albumin. After two consecutive washes in a PBS/1% bovine serum albumin buffer, the cells are either directly analysed in a flow cytometer (FACS Vantage, Becton Dickinson), if the antibody employed is conjugated to a fluorochrome, or labelled with a phycoerythrin-conjugated F(ab')$_2$ fragment of goat anti-mouse IgG immunoglobulin before the FACS analysis. Control aliquots are labelled with a control antibody in order to be able to check non-specific binding to the target cells.

7/NK effector cells:

Peripheral blood mononuclear cells (PBMC) from healthy volunteers (males and females of from 30 to 60 years of age) are obtained using a Ficoll/histopaque density gradient. The NK cells are isolated from the PBMCs as follows:

The CD3$^+$ cells are removed using beads which are coated with anti-CD3 antibody (Dynabeads Dynal, Norway). The beads which are coated in this way are mixed with the peripheral blood mononuclear cells in a beads:target CD3$^+$ cells ratio of 4:1. Following a 30 minute incubation at 4° C., the target cells which have formed complexes with the beads are removed by passage through an appropriate magnetic field.

The fraction devoid of CD3$^+$ cells is then labelled with a phycoerythrin-conjugated anti-CD56 monoclonal antibody in order to select the CD56$^+$ cells by cell sorting using a flow cytometer (FACS).

In order to check the phenotype of the sorted cells (CD56$^+$), a cell sample is immediately labelled either with fluorescein isothiocyanate (FITC)-conjugated anti-CD16 monoclonal antibodies or with a quantum red-conjugated anti-CD3 monoclonal antibody, after which a fluorescence analysis is carried out. The CD56$^+$ population which is obtained is viable (>95%) and exhibits a phenotype which corresponds to NK cells (more than 90% of the NK cells are CD3$^-$, CD16$^+$, CD56$^+$)

9/Cytotoxicity assays:

The cytolytic activity of the peripheral blood mononuclear cells, the NK cells and the YT2C2 cells (effector or E cells) towards the HLA-G transfectants (target or T cells) is assessed by means of 4-hour chromium 51 liberation tests in which the effector cells are mixed with $5.10^3$ chromium 51 (100 μCi of $^{51}$Cr-sodium chromate, Amersham, UK)-labelled target cells, in various E/T ratios, in microtitre plates having a U-shaped bottom.

After 4 hours at 37° C. in a humidified incubator containing 5% $CO_2$, 100 μ of supernatent are removed for liquid-phase scintillation counting (Wallac 1450 Microbeta, Pharmacia, France). The percentage specific lysis is calculated as follows:

percentage specific lysis=[cpm in the experimental well−cpm of spontaneous liberation)/(cpm of maximum liberation−cpm of spontaneous liberation)]×100.

The spontaneous liberation is determined by incubating labelled target cells (T) with the medium. The maximum liberation is determined by solubilizing the target cells in 0.1 M HCl. In all the experiments, the spontaneous liberation is less than 10% of the maximum liberation. The results are presented as means of three samples. In the experiments in which monoclonal antibodies are used to block the HLA-G-NK interaction, the target cells are incubated with the corresponding monoclonal antibody and then washed and incubated with an F(ab')$_2$ goat anti-mouse antibody (Jackson Immunoresearch, USA) in order to avoid the antibody-dependent cell cytotoxicity (ADCC) resulting from interaction of the receptors for the immunoglobulin Fc fragment, which are expressed on the NK cells, with the first antibody employed. The toxicities of the monoclonal antibodies are also checked in each assay and are always less than 3%.

B/RESULTS:

1/Production of stable transfectants which express the HLA-G1 molecule or the HLA-G2 molecule:

Analysis of the transfected HLA-G1 and HLA-G2 cDNA sequences shows that the HLA-G1 cDNA does not contain the two GAC codons corresponding to amino acid positions 247 and 248 (Ellis et al., J. Immunol., 1990, 144, 731–735) but, instead, only one GAC codon corresponding to amino acid position 247 (Pazmany L. et al., Science, 1996, 274, 792–795). The cDNA sequence encoding HLA-G2, which was obtained by RT-PCT amplification using the primers G.53 and G.1225, exhibits a junction between exons 2 and 4 due to the absence of exon 3 in this form of spliced mRNA.

The transfectants are characterized by means of a Southern blot analysis of the RT-PCR products obtained with the parental K562 cell line, the transfectants and the JEG-3 cells using primers G.257 and G.1225. The results are shown in FIG. 2. Hybridization of the resulting RT-PCR products with the G.1200 probe reveals a band of 0.98 kb, in the case of the K562-HLA-G1 transfectant, corresponding to the HLA-G1 mRNA and a band of 0.71 kb corresponding to the alternative spliced form which does not include exon 3 (Kirszenbaum M. et al., Hum. Immunol., 1995, 43, 237–241). In the case of the JEG-3 cells, three bands are observed at 0.98 kb (HLA-G1), 0.7 kb (HLA-G2 and HLA-G4) and 0.43 kb (HLA-G3) (Moreau P. et al., Hum. Immunol., 1997, 52, 41–46). By contrast, no HLA-G band is detected in the parental K562 cell line or in the transfectant control cell line K562-pRc/RSV. Hybridization of the same RT-PCR products with the probe which is specific for exon 3, i.e. G.526, reveals a single band in the transfected HLA-G1 cells, whereas no hybridization is observed in the HLA-G2 transfectants because of the absence of exon 3 in the HLA-G2 form (FIG. 2). RT-PCR amplification of the gene for β-actin, which is constitutively expressed, demonstrates that the absence of HLA-G bands in the K562 controls is not due to the absence of RNA (FIG. 2).

2/Immunoprecipitation and SDS-PAGE analysis of the labelled surface proteins:

The HLA proteins are immunoprecipitated with the monoclonal antibody W6/32 in order to determine whether the transfections result in specific surface expression of the HLA-G proteins. As depicted in FIG. 3, the corresponding Western blot reveals that the W6/32 monoclonal antibody immunoprecipitates a molecule of 39 kDa in the K562 cells which express the HLA-G1 protein (lane 6) and in the JEG-3 cells (lane 10). In the case of the HLA-G2 transfectants, immunoprecipitation with the W6/32 antibody shows a band which corresponds to the size of the G2 protein. No molecule of the HLA system (classic class I HLA molecule, HLA-G1 or HLA-G2) is found either in the parental K562 cells or in the control K562 pRc-RSV cells.

3/Flow cytometry analysis of the HLA-G transfectants:

The flow cytometry profiles of the different cells are analysed in order to determine the level of HLA-G expression at the surface of the cells; the results are depicted in FIG. 4 and relate to the different cell lines studied: i.e. the parental K562 cell line, the control cell line harbouring plasmid pRc/RSV, the HLA-G1 and HLA-G2 transfectants, and the choriocarcinoma cell line JEG-3, which is positive for HLA-G expression. The results which were observed show that the parental K562 cell line does not express any detectable level of HLA class I surface molecule (assessment using the pan-HLA class I antibody W6/32 and using the anti-β2 m antibody B1G6). No HLA class I molecule is detected in the K562 cell line which is transfected with the empty pRc/RSV vector. The HLA-G1 transfectant is labelled with the W6/32 and B1G6 antibodies in almost the same way as that obtained with the JEG-3 cells. The HLA-G2 transfectant is also labelled with the W6/32 antibody and the B1G6 antibody. This result shows that the membrane-linked HLA-G2 isoform is indeed present on the surface of the cells, and associated with β2-microglobulin, in the same way as are the classical class I HLA molecules.

4/Resistance of the HLA-G1 and HLA-G2 transfectants to cytolysis by NK cells:

The HLA-G1 and HLA-G2 transfectants are tested for their sensitivity to NK cells in parallel with the corresponding parental cell line. 20 experiments were carried out, each one of which was recorded using mononuclear cells from different donors. FIG. 5 shows that the lytic activity of the NK cells which were present in the mononuclear cells of the peripheral blood which was isolated from three healthy adult donors is inhibited both by the K562 HLA-G1 transfectants and by the K562 HLA-G2 transfectants whereas the K562 pRc/RSV control cell line remains sensitive to the lytic activity of the NK cells.

Although the absolute level of lysis varies from one donor to another, as depicted in FIG. 5 for the donors designated 4010, 845 and 813, who respectively exhibit high, medium and low levels of lysis, the sensitivity of the cells expressing the HLA-G1 molecule and the HLA-G2 molecule is reduced by at least 70%. These results are confirmed when use is made, as effector cells, of the polyclonal NK $CD3^-$, $CD16^+$, $CD56^+$ cells which were obtained from mononuclear cells of the peripheral blood of three other donors (FIG. 6). Furthermore, no difference is observed between male and female donors.

In order to demonstrate that the inhibition of the lytic activity of the NK cells is in fact due to the presence of the HLA-G1 and HLA-G2 molecules on the surface of the target cells, cytotoxicity tests are carried out in the presence of target cells which have been preincubated either with the W6/32 antibody, which recognizes the HLA-G1 and HLA-G2 molecules, or with a control antibody. The addition of the W6/32 monoclonal antibody relieves the inhibition of the activity of the NK cells which is due to the presence of the HLA-G1 and HLA-G2 molecules and, as a consequence, restores the lytic activity of the NK cells on the transfected target cells (FIGS. 7a and 7b). Since the mechanism of antibody-dependent cell cytotoxicity (ADCC) could be involved in this reaction as a result of interaction with the Fc fragment receptors of the NK cells, the Fc fragment of the W6/32 antibody is blocked with an $F(ab')_2$ fragment from goat anti-mouse IgG antibody.

5/Inhibition, by the HLA-G1 and HLA-G2 transfectants, of the lysis which is induced by clone YT2C2 having NK activity:

Clone YT2C2, corresponding to immature leukaemic T cells, is used as the effector against the HLA-G transfectants. FIG. 8 shows that while both the HLA-G1 and the HLA-G2 transfectants abolish the lysis which is induced by the YT2C2 clone, the control cell lines do not do this. However, contrary to what is observed with the peripheral blood mononuclear cells, the inhibition of the lysis induced by clone YT2C2 is not relieved by using transfected target cells which have been treated with W6/32 monoclonal antibody (FIG. 7c), suggesting that the epitope on the HLA-G molecule which is recognized by the monoclonal antibody is not involved in recognition of the HLA-G molecule by the receptor which is present on the YT2C2 cells.

An indirect immunofluorescence analysis is carried out in order to check the phenotype of the YT2C2 cells. In order to do this, use was made of the monoclonal antibodies EB6 and GL183, which respectively recognize the NKIR1 and NKIR2 receptors which are expressed on the surface of NK cell subgroups, and of the antibody HP-3B1, which recognizes the CD94 receptor which is expressed on most NK cells. These receptors are involved in the recognition of the HLA-A, -B or -C molecules by the NK cells (Colonna et al., Science, 1995, 268, 405–408 and Moretta et al., J. Exp. Med., 1994, 180, 545–555). FIG. 8 shows that the YT2C2 cells exhibit the following negative phenotype: $EB6^-$, $GL183^-$ and $HP3B1^-$. These monoclonal antibodies were previously tested by indirect immunofluorescence and positively label from 3 to 10% of the peripheral blood mononuclear cells from healthy adult donors. These various results demonstrate that, in addition to the receptors designated NKIR1 and NKIR2, which were recently reported to recognize HLA-G (Pazmany et al., (1996) (loc. cit.), clone YT2C2 expresses a novel receptor which is capable of binding HLA-G molecules and of inducing protection against lysis by the YT2C2 cells.

The results taken as a whole demonstrate that the HLA-G antigens play a role in protecting cells which express these molecules on their surface against the cytotoxicity which is induced by NK cells. Contrary to the studies of the prior art (Chumbley et al., Cell Immunol., 1994, 155, 312–322, Deniz et al., J. Immunol., 1994, 152, 4255–4261 and Pazmany L. et al., (1996) (loc. cit.), in which it was proposed to transfect the genomic DNA encoding the HLA-G molecule into a target cell in order to study its effects on the lytic activity of an NK clone, the inventors have found that, by separately assessing the HLA-G1 and HLA-G2 isoforms, under physiological conditions, vis-á-vis polyclonal NK cells obtained from healthy adult donors, it was surprisingly possible: (i) to express the HLA-G1 and HLA-G2 molecules at the surface of the target cells and (ii) to show that these target cells, which had been modified in this way, were able to inhibit the lytic activity of the said NK cells.

Table I below demonstrates that, when bound to the cell membrane, both the HLA-G1 isoform and the HLA-G2 isoform strongly inhibit the lysis which is induced by NK cells.

TABLE I

| Cell line | mRNA transcript HLA-G1 | mRNA transcript HLA-G2 | Membrane expression of the class I HLAs W6/32 | Resistance to NK lysis |
| --- | --- | --- | --- | --- |
| Untransfected |   |   |   |   |
| K562 | − | − | − | − |
| Transfected |   |   |   |   |
| K562-pRc/RSV | − | − | − | − |
| K562-HLA-G1 | + | − | + | + |
| K562-HLA-G2 | − | + | + | + |

This inhibition is relieved when the transfected cells which express the HLA-G1 molecule or the HLA-G2 molecule are incubated with the pan-class I monoclonal antibody, indicating that inhibition of the lysis induced by the NK cells is due to the presence of the HLA-G molecules on the surface of the transfected K562 target cells (FIG. 7). The fact that the lytic NK activity is inhibited by the HLA-G-positive target cells in the case of all the donors tested confirms that the HLA-G molecule could be the common ligand for the inhibitory NK receptor which is present in all individuals (NKIR) and demonstrates the importance of obtaining cells which exhibit a substantial and predictable level of HLA-G molecule expression.

Surprisingly, it follows from these results that the α1 domain which is common to these two isoforms should be regarded as playing an important role in protection against NK cells. This view can be supported by the fact that the amino acid sequences of the class I HLA molecules which are required for the interaction with the KIR receptor are located in the α1 domain (Colonna et al., Proc. Natl. Acad. Sci., 1992, 89, 7983–7985 and Mandelboim et al., J. Exp. Med., 1996, 184, 913–922). Sequential analysis shows that the α1 domain of the HLA-G molecules exhibits amino acids which were previously reported to induce resistance, in the HLA-A, HLA-B and HLA-C protective alleles, to the cytolysis which is induced by NK cells (Pazmany et al., loc. cit.). Surprisingly, the inventors have now found that the HLA-G molecule shares structural features with the HLA-A3, A11, Aw68, Aw69, B7 and B27 protective alleles. In particular, position 74 in the α1 domain of HLA-G is occupied by an Asp residue which is associated with the induction of resistance to NK cells.

The inventors furthermore found, equally surprisingly, that YT2C2 leukaemic T cells no longer induced lysis in the presence of transfectants expressing the HLA-G1 molecule or the HLA-G2 molecule even though no KIR receptors capable of binding HLA-G (p58.1 receptor, p58.2 receptor and CD94) are present in the YT2C2 cells (FIG. 8). These results suggest that a novel receptor which is distinct from the previously described receptors is involved in recognizing the HLA-G1 and HLA-G2 molecules.

EXAMPLE 2
Demonstration of the Inhibitory Activity of the HLA-G Isoforms in the Proliferative Allogeneic Response A mixed culture is prepared from mononuclear cells which derive from the peripheral blood of two volunteer donors who exhibit different HLA class II antigens. The cells from one donor, termed stimulatory cells, were irradiated at 3000 rads to prevent them proliferating. Only the responder cells of the other individual are able to proliferate.

Either K562 cells harbouring plasmid pRc/RSV, as a control (no expression of MHC antigen), or K562 cells which are transfected with, and express on their surface, an HLA-G isoform, for example the HLA-G1 isoform (insertion of plasmid pRc/RSV-G1), are introduced into these cultures. The K562 cells were irradiated in order to prevent any proliferation.

FIG. 9 depicts the results which were obtained: an inhibition, of the order of 50 to 67%, of the proliferative allogeneic response is observed with four different donors.

EXAMPLE 3
Inhibition of NK Activity by the HLA-G5 Protein

When expressed by a eukaryotic cell according to the invention, or directly injected, the HLA-G5 protein, like the other HLA-G isoforms, inhibits the cytolytic activity of NK cells.

This inhibition is dose-dependant, as shown by FIGS. 10 and 11, which represent the result of assays which were carried out using a GST-HLA-G5 fusion protein which was expressed in E. coli. After having been extracted from bacterial cultures (centrifugation, recovery of the pellet in an STE buffer, lysis of the cells with 1.5% N-lauroylsarcosine, clarification of the lysate by centrifugation and solubilization of the supernatant with 2% Triton X-100), this fusion protein is purified on a glutathione-Sepharose column (Pharmacia Biotech) or by affinity chromatography using anti-HLA antibodies or anti-GST antibodies.

The cytotoxicity assays are carried out as specified above, using K562 cells, which are sensitive to NK cells, as the positive control.

14 experiments, performed on mononuclear cells from different donors, are carried out in the presence of GST-HLA-G5 or Sepharose-GST-HLA-G5.

FIG. 10 shows that the lytic activity of the PBMCs isolated from three healthy adult donors is inhibited by Sepharose-GST-HLA-G5 beads; FIG. 11 confirms that the soluble protein exhibits the same inhibitory activity on the lysis induced by NK cells as do the other isoforms.

EXAMPLE 4
Factors Involved in the Stimulation of the Transcription of the Different HLA-G Isoforms.

RNase protection test
A/MATERIALS AND METHOD
Radioprobes:
Radio-labelled single-stranded cRNA probes are synthesized using a MAXIScript® (Ambion) transcription kit in the presence of T7 RNA polymerase and 5 µl of ($\alpha$-$^{32}$p) CTP (Amersham), in accordance with the manufacturer's instructions.

A cyclophilin template is supplied by the manufacturer (Ambion). An HLA-G template is obtained by chain (PCR) amplification of a genomic HLA-G fragment corresponding to part of the untranslated region (3' UT region). The following primers are employed:

sense primer (G.1089F):
5'-CCCTTTGTGACTTCAAGAAC (SEQ ID NO: 1)
anti-sense primer (T7G.1250R):
5'-GGATCCTAATACGACTCACTATAGGGAGGTTATAGCTCAGTGGCCCAC (SEQ ID NO: 2)

This primer contains a sequence which makes it possible to generate a T7 promoter during the PCR (part printed in bold).

The probes are purified by electrophoresis for approximately 1 h at 200 V on a 6% acrylamide+8 M urea gel.

After the electrophoresis, the gel is exposed to an X-ray-sensitive film.

The area of the gel containing the complete labelled transcript is immersed in 350 µl of probe elution buffer (Ambion kit).

Method:

The HLA-G transcripts are protected in conformity with the HybSpeed® RPA kit (Ambion), in accordance with the manufacturer's recommendations.

5 µg of total RNA are isolated using the RNA NOW reagent (Ozyme) in accordance with the manufacturer's recommendations; 5.10$^5$ cpm of HLA-G riboprobe and 5.10$^5$ cpm of cyclophilin riboprobe are hybridized for 10 min in a HybSpeed® hybridization buffer.

An RNAse A/T mixture, at a ¹/₁₀₀th final concentration, is added for 30 seconds. These protected and radiolabelled fragments are precipitated and separated on a 5% acrylamide: bisacrylamide (19:1) gel (100 V).

The gel is dried and exposed (Biorad) in order to quantify the HLA-G signal.

The values are compared to the signals obtained with the cyclophilin.

B/RESULTS

Various hormones and cytokines increase transcription of the HLA-G molecule. FIGS. 12 and 13 depict the results which were obtained after incubating trophoblasts or eukaryotic cells, which were expressing at least one HLA-G isoform, for 72 hours with the following different factors: interleukin 10, interleukin 1β, interferon γ, TGF-β, EGF, prolactin, β-oestradiol, hydrocortisone and dexamethasone.

These figures illustrate the increase in mRNA transcription, as measured by the RPP technique.

These FIGS. 12 and 13 show, in particular, that the increase with regard to the trophoblasts, in the presence of culture media and without any stimulation, is from 2× to 7.3×, particularly in the case of the IL 10, IL 1β, TGF β and the glucocorticoids.

These results demonstrate, in particular, the importance of the products according to the invention in preventing spontaneous repeated abortions.

As follows from the above, the invention is in no way limited to those of its embodiments which have just been described more explicitly; on the contrary, it encompasses all the variants of which the skilled person can conceive without departing from the context or the scope of the present invention.

---

---

What is claimed is:

1. A eukaryotic cell, which is obtained by genetic modification, which is transfected with an expression vector which contains at least one cDNA encoding an HLA-G isoform which is selected from the group consisting of the HLA-G4, HLA-G5 and HLA-G6 isoforms.

2. A eukaryotic cell which is obtained by genetic modification, which is transfected with an expression vector which contains a suitable origin of replication, a selection marker such as a gene for resistance to an antibiotic, the RSV viral promoter and a cDNA which encodes an HLA-G isoform which is selected from the group consisting of the HLA-G4, HLA-G5 and HLA-G6 isoforms.

3. The eukaryotic cell according to claim 2, wherein said cDNA encodes an isoform which contains at least one extracellular domain.

4. The eukaryotic cell according to claim 2, wherein said cDNA encodes an isoform which contains at least one extracellular domain.

5. The eukaryotic cell according to claim 3, wherein said at least one extracellular domain is the α1 domain.

6. The eukaryotic cell according to claim 4, wherein said at least one extracelluar domain is the α1 domain.

7. A vector comprising a cDNA encoding a HLA-G isoform selected from the group consisting of the HLA-G4, HLA-G5 and HLA-G6 isoforms.

* * * * *

UNITED STATES PATENT AND TRADEMARK OFFICE
CERTIFICATE OF CORRECTION

PATENT NO. : 6,528,304 B1
DATED : March 4, 2003
INVENTOR(S) : Edgardo Delfino Carosella et al.

It is certified that error appears in the above-identified patent and that said Letters Patent is hereby corrected as shown below:

Column 17,
Line 3, "claim 2" should read -- claim 1 --.

Signed and Sealed this

Twenty-seventh Day of April, 2004

JON W. DUDAS
*Acting Director of the United States Patent and Trademark Office*